(12) United States Patent
Armstrong et al.

(10) Patent No.: US 8,080,062 B2
(45) Date of Patent: Dec. 20, 2011

(54) INTERVERTEBRAL IMPLANT WITH FIXATION MECHANISM

(75) Inventors: William D Armstrong, Memphis, TN (US); Gary S. Lindemann, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 481 days.

(21) Appl. No.: 12/326,682

(22) Filed: Dec. 2, 2008

(65) Prior Publication Data
US 2010/0137989 A1 Jun. 3, 2010

(51) Int. Cl.
*A61F 2/44* (2006.01)
(52) U.S. Cl. .................................. 623/17.11
(58) Field of Classification Search ............... 623/17.13, 623/17.15, 17.16; 411/34, 37, 38
See application file for complete search history.

(56) References Cited

U.S. PATENT DOCUMENTS

| | | | |
|---|---|---|---|
| 5,171,278 A | 12/1992 | Pisharodi | |
| 5,390,683 A | 2/1995 | Pisharodi | |
| 5,554,191 A | 9/1996 | Lahille et al. | |
| 5,609,635 A * | 3/1997 | Michelson | 623/17.16 |
| 5,658,335 A | 8/1997 | Allen | |
| 6,113,638 A | 9/2000 | Williams et al. | |
| 6,371,989 B1 | 4/2002 | Chauvin et al. | |
| 6,500,205 B1 | 12/2002 | Michelson | |
| 6,652,584 B2 | 11/2003 | Michelson | |
| 6,716,247 B2 | 4/2004 | Michelson | |
| 6,723,126 B1 | 4/2004 | Berry | |
| 6,746,191 B2 * | 6/2004 | Edland | 411/34 |
| 6,793,679 B2 | 9/2004 | Michelson | |
| 6,808,537 B2 | 10/2004 | Michelson | |
| 6,890,355 B2 | 5/2005 | Michelson | |
| 6,955,691 B2 | 10/2005 | Chae et al. | |
| 6,962,606 B2 | 11/2005 | Michelson | |
| 7,008,453 B1 | 3/2006 | Michelson | |
| 7,070,598 B2 | 7/2006 | Lim et al. | |
| 7,087,243 B2 | 8/2006 | Edgren et al. | |
| 7,118,598 B2 | 10/2006 | Michelson | |
| 7,214,243 B2 | 5/2007 | Taylor | |
| 7,217,293 B2 | 5/2007 | Branch, Jr. | |
| 7,326,251 B2 | 2/2008 | McCombe et al. | |
| 2001/0034553 A1 | 10/2001 | Michelson | |
| 2002/0052656 A1 | 5/2002 | Michelson | |
| 2002/0072801 A1 | 6/2002 | Michelson | |
| 2002/0116066 A1 | 8/2002 | Chauvin et al. | |
| 2002/0128717 A1 | 9/2002 | Alfaro et al. | |
| 2003/0050701 A1 | 3/2003 | Michelson | |
| 2003/0060825 A1 | 3/2003 | Alfaro et al. | |
| 2003/0208275 A1 | 11/2003 | Michelson | |
| 2004/0254644 A1 | 12/2004 | Taylor | |
| 2006/0241621 A1 | 10/2006 | Moskowitz et al. | |
| 2006/0247770 A1 | 11/2006 | Peterman | |
| 2007/0049943 A1 | 3/2007 | Moskowitz et al. | |

\* cited by examiner

*Primary Examiner* — David Isabella
*Assistant Examiner* — Brian Dukert

(57) ABSTRACT

The present application is directed to implants for positioned between vertebral members. The implant may include a superior surface to contact against a first vertebral member, and an inferior surface to contact against a second vertebral member. The implant includes a fixation mechanism that is operable to extend a portion of the fixation mechanism into the vertebral members immediately above and below the implanted implant to affix the implant within the vertebral space between such vertebral members. The implant is substantially open in the superior and inferior directions to allow for the introduction of bone growth material within the interior of the implant to help promote fusion between the vertebral members.

18 Claims, 5 Drawing Sheets

US 8,080,062 B2

INTERVERTEBRAL IMPLANT WITH FIXATION MECHANISM

BACKGROUND

The present application relates generally to vertebral implants and methods of use, and more particularly to an implant having a retaining feature preventing inadvertent removal of the implant from the intervertebral space.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation of the vertebral members.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

It is known that if an intervertebral disc is damaged, it can be removed and the resulting space between the two adjacent vertebrae may be filled with a bone growth inducing substance to promote a boney fusion across the disc space. Fixation devices external to the disc space have been utilized to maintain the position of the adjacent vertebrae while the intervening material fuses with adjacent bone to form a boney bridge. As an alternative or in conjunction with fixation devices, load bearing spacers, such as artificial devices or bone grafts, may be placed in the empty disc space. These spacers transmit the loading from one adjacent vertebra to the other adjacent vertebra during the healing process. Such spacers may be provided in a variety of forms.

A need exists for improvements to existing interbody spacers and the present invention is directed to such need.

SUMMARY

The present application is directed to implants that fit within an intervertebral space formed between first and second vertebral members. The implant may include a generally rectangular body which is open on the superior (top) end and inferior (bottom) end and having a fixation mechanism provided therein. The body may include an exterior perimeter which is generally "D" shaped. The body may further include a height defined by a superior surface that contacts the first vertebral member and an inferior surface that contacts the second vertebral member. The implant includes a fixation mechanism that is operable to extend a portion of the fixation mechanism into the vertebral members immediately above and below the implanted implant to affix the implant within the vertebral space between such vertebral members.

In an embodiment, the fixation mechanism includes a screw having a collar adjacent the head of the screw positioned through the anterior wall of the body, the screw traversing the inside of the implant to the position adjacent the posterior wall of the body. It may be desirable for the end of the screw to be embedded into a portion of the posterior wall, or conversely, the end of the screw is left free standing within the interior of the implant. An internally threaded ring is provided on the threads of the screw, the fixation mechanism having a pair of diametrically opposed flexible arms wherein one end of each of the arms are attached to the ring and the opposite ends of each of the arms being attached to the collar adjacent the head of the screw. The collar is affixed to the inside wall of anterior wall of the body. The arms are provided with a bendable portion such that upon rotation of the screw a portion of the diametrically positioned arms extend outwardly of the superior and inferior surfaces of the implant to extend into the first and second vertebral members, respectively, to affix the implant within the intervertebral space between the first and second vertebral members.

DETAILED DESCRIPTION

Figure 1:
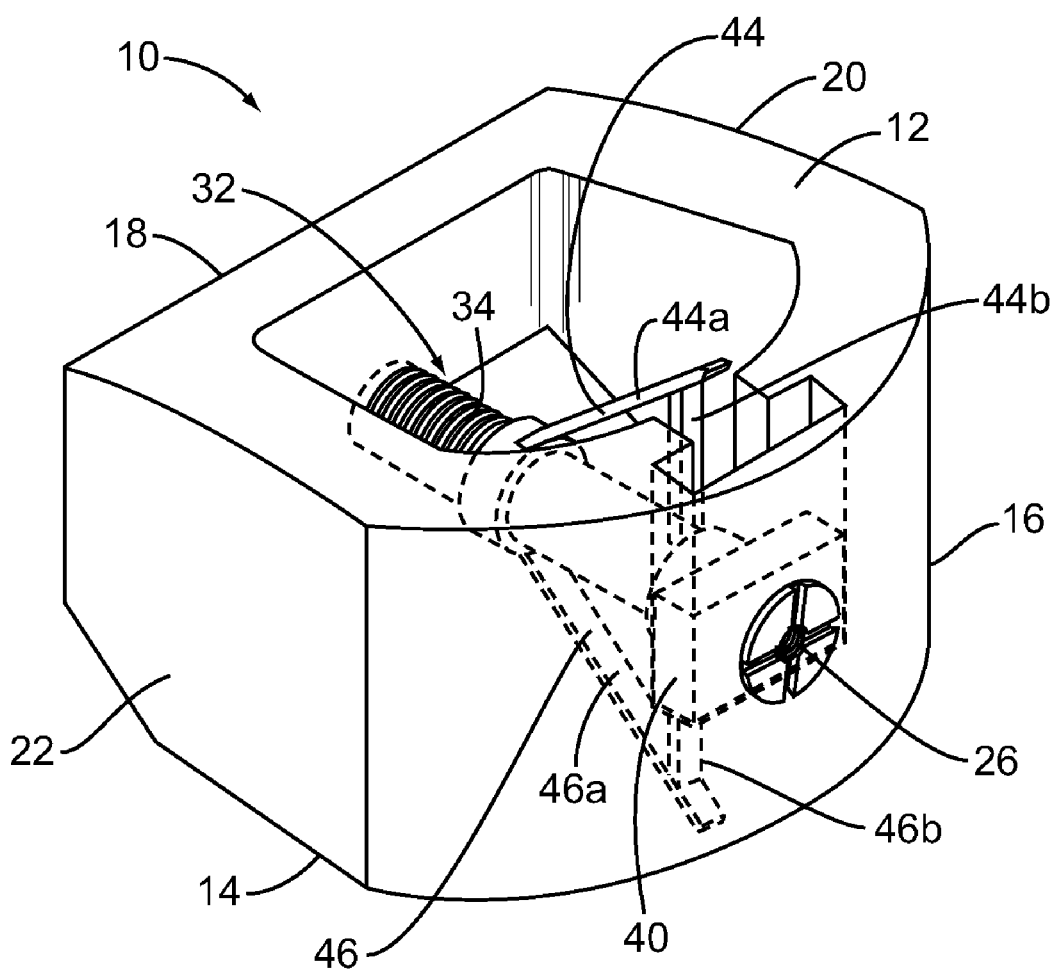
FIG. 1 is a perspective view of an implant according to the present invention.

The present application is directed to implants for positioning within an intervertebral space formed between first and second vertebral members. FIG. 1 illustrates one embodiment of an implant 10 having a superior surface 12 to contact against a first vertebral member, and an inferior surface 14 to contact against a second vertebral member. The implant 10 includes a generally "D" shaped perimeter having a rounded anterior wall 16 and a generally flat posterior wall 18 connected by a pair of lateral walls 20 and 22. It may be desirable for the lateral walls 20 and 22 to converge slightly from the ends of the anterior wall 16 to the ends of the posterior wall 18. However, it may also be desirable for the lateral walls 20 and 22 to be parallel to one another or even converging slightly from the posterior wall 18 to the ends of the anterior wall 16.

As generally referred to herein, superior and inferior directions refer to upward and downward directions, respectively, assuming a person is standing upright. Anterior and posterior directions refer to forward and rearward directions, respectively, assuming a person is standing upright.

Figure 2:
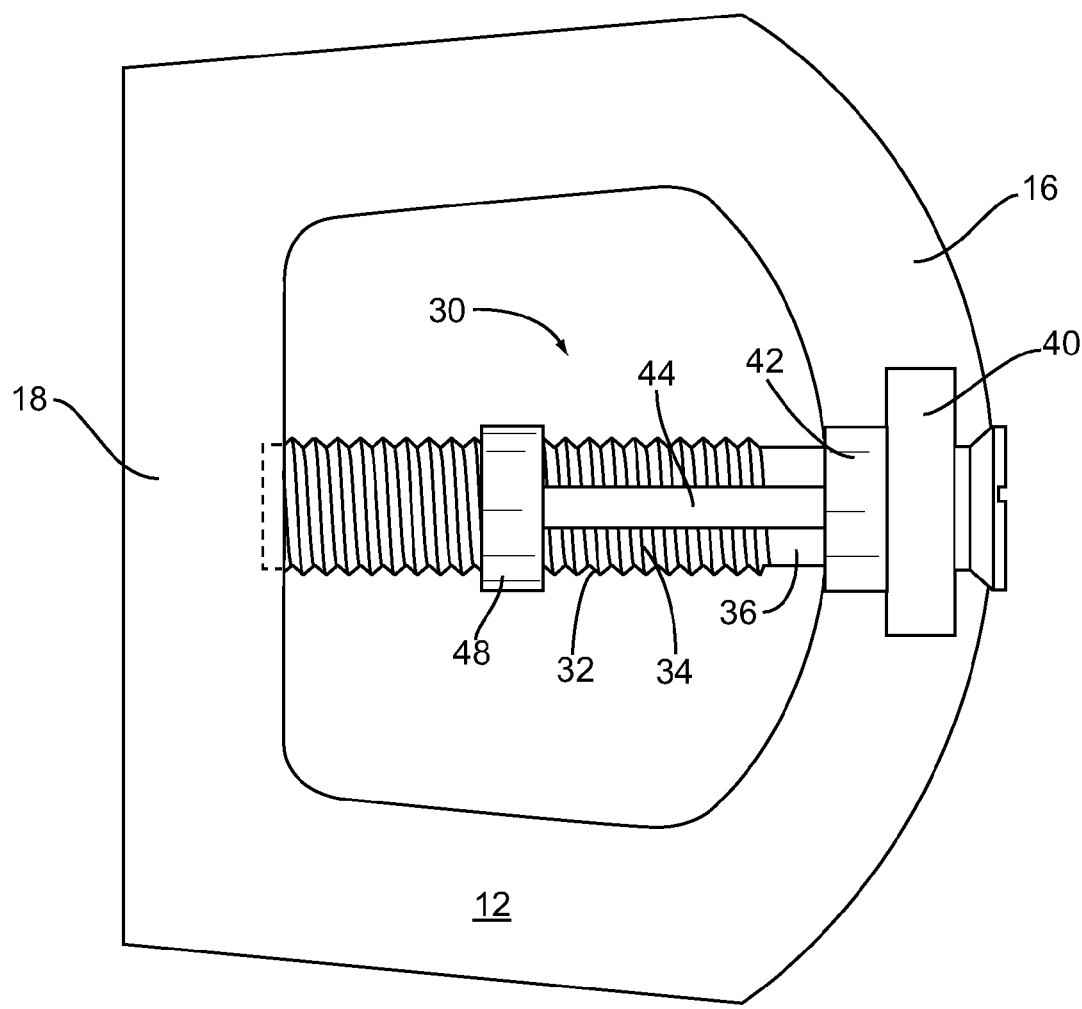
FIG. 2 is a top view of the implant of FIG. 1.

As shown in FIGS. 1 and 2, the fixation mechanism 30 is shown in the interior of the implant 10. Other than the fixation mechanism 30 the interior space of the implant 10 is left largely open such that boney ingrowth from the first and second vertebral members can grow into and through the interior space of the implant 10. The interior space can be filled and hold any natural or artificial osteoconductive, osteoinductive, osteogenic, or other fusion enhancing material. Some examples of such materials are bone harvested from the patient, or bone growth inducing material such as, but not limited to, hydroxyapatite, hydroxyapatite tricalcium phosphate; bone morphogenic proteins; or associate carrier materials for any of the above. The implant 10 itself is made of material appropriate for human implantation, such as titanium, PEEK, other polymers, composites, or other biocompatible metals such as stainless steel, tantalum, ceramic, chrome cobalt, or resorbable polymers, and/or may be made of, and/or filled, and/or coated with a bone ingrowth inducing material such as, but not limited to, hydroxyapatite or hydroxyapatite tricalcium phosphate or any other osteoconductive, osteoinductive, osteogenic or other fusion enhancing material.

Figure 3:
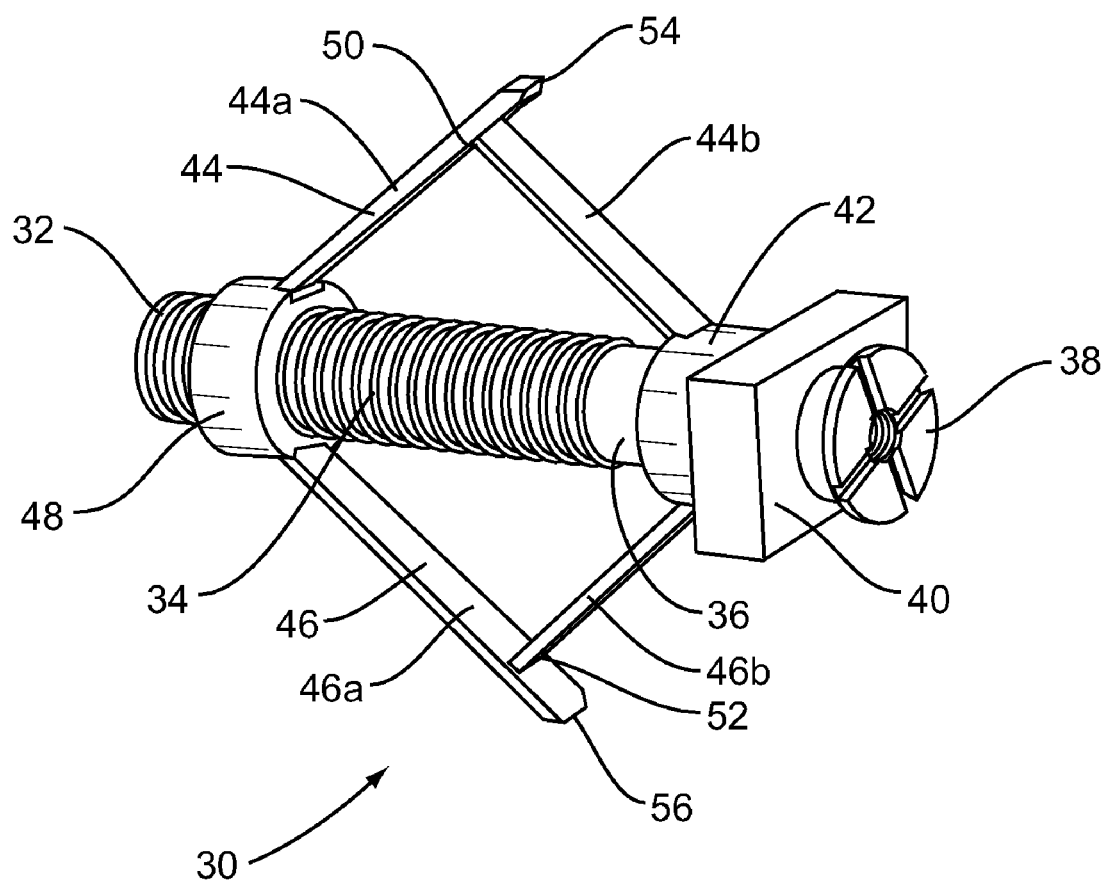
FIG. 3 is a perspective view of the internal fixation mechanism according to the present invention.
Figure 6:
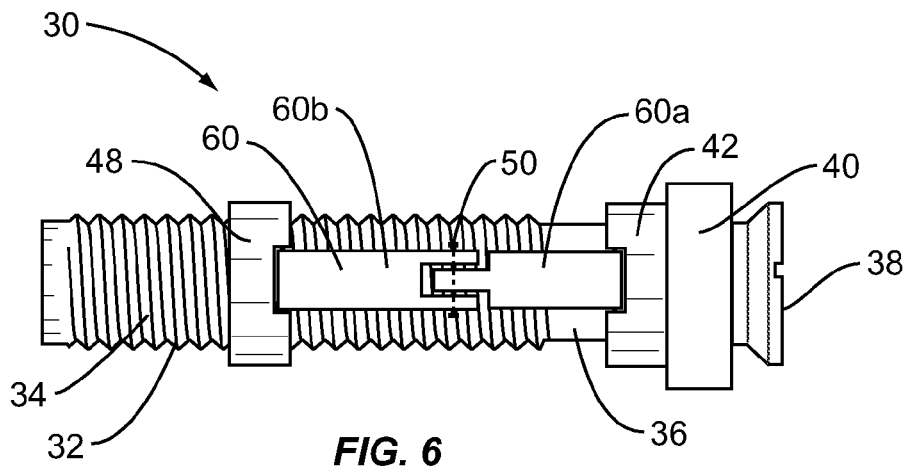
FIG. 6 is top view of another embodiment of the fixation mechanism shown in FIG. 3.
Figure 7:
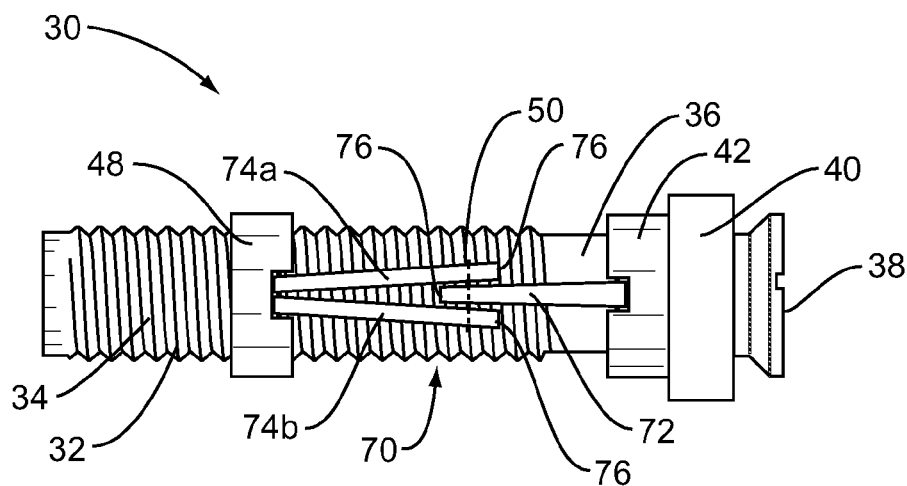
FIG. 7 is a top view of yet another embodiment of the fixation mechanism shown in FIG. 3.
Figure 8:
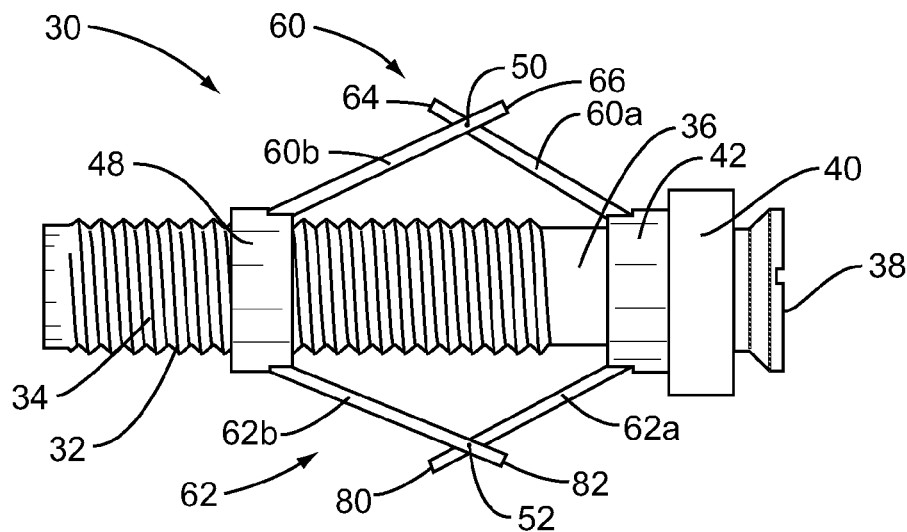
FIG. 8 is a side view of the fixation mechanism shown in FIG. 6.

An embodiment of the fixation mechanism 30 is shown in FIG. 3, separate and apart from the implant 10. FIGS. 1 and 2 show the fixation mechanism 30 in position within the interior space of the implant 10. In FIG. 3, the fixation mechanism 30 is shown having a screw shaft 32 with a threaded portion 34 and a non-threaded portion 36. A screw head 38 adapted to be turned with either a Phillips head, slotted head, or Allen head screwdriver, or any other effective turning mechanism is provided on an end of the shaft 32 adjacent the non-threaded portion 36. A generally rectangular collar or block 40 is positioned about the screw shaft adjacent the screw head 38, the block 40 having a cylindrical flange 42 extending toward the threaded portion 34 of the screw shaft. A cylindrical ring 48 having internal threads is threaded unto the threaded portion 34 of the screw shaft and is initially positioned near the end of the screw shaft opposite the screw head 38. A pair of diametrically opposed hinged arms 44 and 46 are provided extending between the flange 42 and the cylindrical ring 48. The arms 44 and 46 of the illustrated embodiment are hinged at the flange 42 as well as at the ring 48. The arms 44 and 46 are each provided with two arm segments 44a, 44b, and 46a, 46b, respectively, and each of the arms is provided with a hinge 50 and 52 between the arm segments 44a and 44b and 46a and 46b, respectively. One or both of the arm segments may have a barb 54 and 56 extending from a length of the arm segment 44a or 44b, and 46a or 46b (as shown in FIG. 3, the barbs 54 and 56 extend from arm segments 44a and 46a) such that the barb overlaps a portion of the other arm segment when such segments are in a generally parallel orientation. However, alternatively, the barbs 54 and 56 could extend from the other arm segments 44b and 46b or even alternatively be opposite such that barb 54 extends from arm segment 44a and barb 56 extends from arm segment 46b. FIGS. 6-8, more fully discussed below, depict various additional embodiments.

In reference to FIGS. 1, 2, 4, and 5, the fixation mechanism 30 is shown in position within the spinal implant 10. The block or collar 40 is affixed within the anterior wall 16 with the head 38 of the screw extending through the anterior wall 16 so as to be operated by a screw driver from outside the anterior wall 16 of the implant 10. The fixation mechanism 30 extends through the interior of the implant such that the other end of the screw opposite the head 38 is embedded into or positioned adjacent or near the interior surface of the posterior wall 18 of the implant 10. The screw head 38 also has a threaded hole 26 which can receive an installation tool (not shown) for positioning the implant 10 within the vertebral space.

Figure 4:
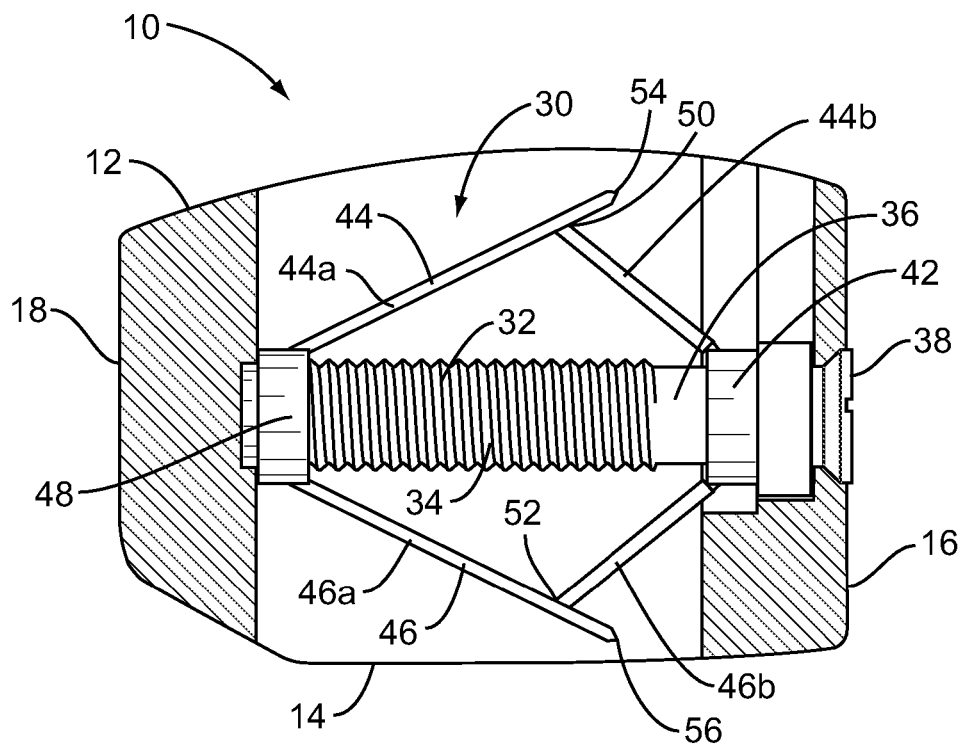
FIG. 4 is a side view of an implant according to the present invention showing the fixation mechanism in the collapsed position.
Figure 5:
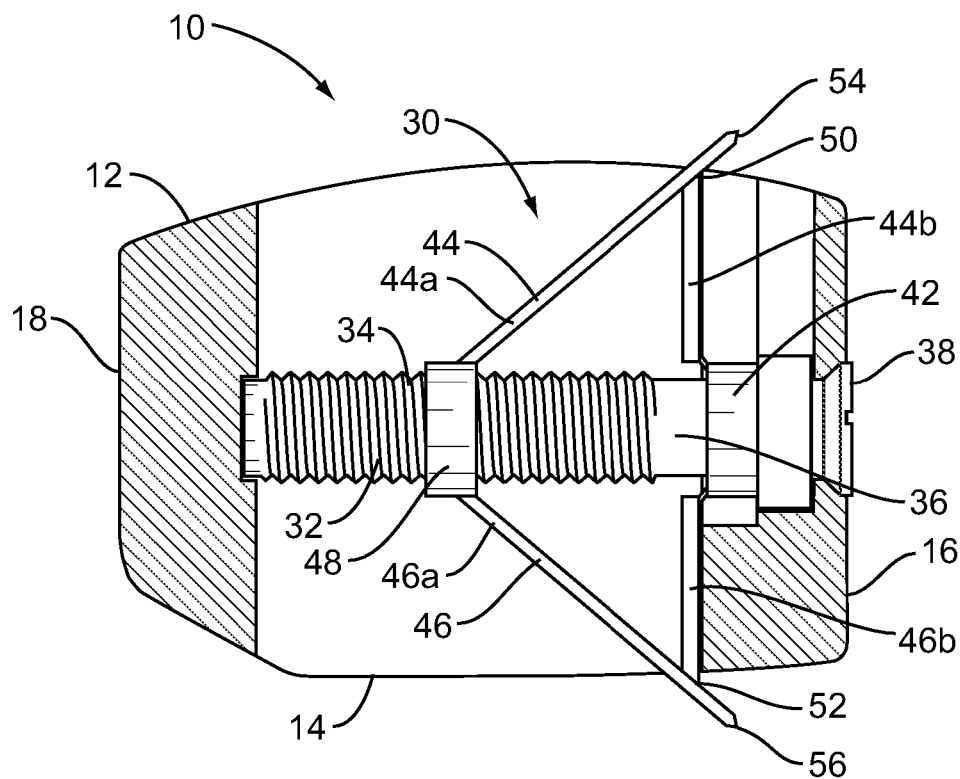
FIG. 5 is a side view of an implant according to the present invention showing the fixation mechanism in the expanded position.

In operation and as shown in FIGS. 3, 4, and 5, when the screw is rotated in a clockwise direction the cylindrical ring 48 moves towards the screw head 38, thereby spreading the arms 44 and 46 radially away from the screw shaft 32. The hinge 50 and 52 of arms 44 ad 46, respectively, allows the arm segments 44a-44b and 46a-46b to become non-parallel such that as the hinge 50 and 52 move transversely away from the screw shaft 32, the barbs 54 and 56 extend outwardly away from hinges 50 and 52. Referring to FIG. 4, the diametrically opposed arms 44 and 46 are shown in the parallel position adjacent the screw shaft 32. And, referring to FIG. 5, the arms 44 and 46 are shown in their fully extended position such that the barbs 54 and 56 are extending outside the implant 10 such that they would be extending into the vertebral body members both above and below the implant 10 when it is positioned within an intervertebral space formed between first and second vertebral members.

Referring to FIGS. 6 and 8, in another embodiment, the fixation mechanism 30 is shown separate and apart from implant 10. The fixation mechanism 30 is shown having a screw shaft 32 with a threaded portion 34. A screw head 38 adapted to be turned by a Phillips head, slotted head, Allen head screwdriver, or any other effective turning mechanism is provided on an end of the shaft 32. A generally rectangular collar or block 40 is positioned about the screw shaft adjacent the screw head 38, the block 40 having a cylindrical flange 42 extending toward the threaded portion 34 of the screw shaft. A cylindrical ring 48 having internal threads is threaded unto the threaded portion 34 of the screw shaft and is initially positioned near the end of the screw shaft opposite the screw head 38. A pair of diametrically opposed hinged arms 60 and 62 (not shown in FIG. 6, on opposite side of mechanism from arm 60) are provided extending between the flange 42 and the cylindrical ring 48. The arms 60 and 62 of the embodiment of FIGS. 6 and 8, are hinged at the flange 42 as well as at the ring 48. The arms 60 and 62 are provided with two arm segments 60a, 60b, and 62a, 62b, respectively, and each of the arms is provided with a hinge 50 and 52 between the arm segments 60a and 60b and 62a and 62b, respectively. In this embodiment both of the arm segments have barbs 64 and 66 extending from a length of the arm segments 60a and 60b, and barbs 80 and 82 extending from a length of the arm segments 62a or 62b such that the barbs overlaps a portion of the other arm segment when such segments are in a parallel orientation.

Referring to FIG. 7, another embodiment of the fixation mechanism 30, is shown separate and apart from implant 10. The fixation element 30 is very similar to that discussed above in selection of FIG. 6. In the embodiment of FIG. 7, the various parts of the fixation mechanism 30 are numbered the same as FIG. 6, except that the diametrically opposed arms 70 and 72 (arm 72 not shown, mechanism will be described in relation only to arm 70). Arm 70 is hinged at the flange 42, as well as at the ring 48. Arm 70 is provided with two arm segments 72 and 74. The arm segments 72 and 74 are hinged at 50. Arm 74 is split into a "v" with two arm segments 74a and 74b so that a portion of each arm segment 74a and 74b extend on either side of arm 72 adjacent hinge 50. Barbs 76 extend from each of the arm segments 72, 74a and 74b. In this fashion, when the fixation mechanism 30 of FIGS. 6, 7, and 8 are positioned within the implant 10 as shown generally in FIGS. 1 and 2, the barbs are operable to extend outside the boundaries of the implant 10 to bite into the vertebral members both above and below the implant 10 when it is positioned within an intervertebral space formed between first and second vertebral members.

The implant 10 of the present invention may be placed within an intervertebral space between first and second vertebral members within the cervical spine. In some embodiments, the implant 10 may also be used within the lumbar spine area as well.

The implant 10 may be inserted into the intervertebral space from a variety of directions. In one embodiment, the implant 10 is inserted in an anterior approach with the screw head 38 extending through and being operable through the anterior wall 16 of the implant. Other applications contemplate other approaches, including posterior, postero-lateral, antero-lateral and lateral approaches to the spine, and accessing other regions of the spine, including the cervical, thoracic, lumbar and/or sacral portions of the spine. In each such application the fixation mechanism 30 would be repositioned with the spinal implant 10 such that the screw head 38 would pass through the spinal implant wall facing the approach taken for insertion within the vertebral space (i.e., if postero-lateral approach, the screw head 38 would extend through the wall of the implant 10 adjacent the postero-lateral approach).

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An implant to fit within an intervertebral space formed between first and second vertebral members, the implant comprising:
    a body having a walled perimeter being substantially open at its superior and inferior ends, the body including a height defined by a superior surface that contacts the first vertebral member and an inferior surface that contacts the second vertebral member; and
    a fixation mechanism, comprising:
        a screw having a screw head extending through a wall of the walled perimeter of the body and a threaded shaft extending into the interior of the body:
        an internally threaded ring provided about the threaded shaft of the screw; and
        a pair of arms hingedly connected to the ring, the pair of arms being diametrically disposed about the screw shaft in superior and inferior directions;
    such that upon rotation of the screw head from outside the implant, the ring moves toward the screw head thereby causing the pair of arms to move from a first position wherein the arms are within the walled perimeter of said body to a second position wherein a portion of said arms extend outside the walled perimeter of said body in the superior and inferior directions such that said portions of said arms extend into the first and second vertebral members to affix said implant within the intervertebral space therebetween.

2. The implant of claim 1, wherein the screw is provided with a non-threaded portion adjacent the screw head and a threaded portion distal to the non-threaded portion, a collar is provided about the non-threaded portion of the screw, said collar being affixed to the wall of the implant such that the head of the screw extends through said wall, each of the arms being hingedly connected to the collar and ring, each of the arms being provided with first and second arm segments hingedly connected together such that upon rotation of the screw head the ring moves toward the screw head such that each of the arms extend radially away from the screw shaft so that a portion of said arm segments extend outside the perimeter of the implant when the arms are in the second position.

3. The implant of claim 2, wherein a portion of each arm segment that extends outside the perimeter of the implant when in the second position is provided with a barb that can bite into the first and second vertebral members adjacent the implant to affix the implant within the vertebral space therebetween.

4. The implant of claim 1, wherein the screw head extends through an anterior wall of the implant such that the screw extends towards a posterior wall of the implant.

5. The implant of claim 1, wherein the screw head extends through a posterior wall of the implant such that the screw extends towards an anterior wall of the implant.

6. The implant of claim 1, wherein the screw head extends through a transverse wall of the implant such that the screw extends towards an opposite transverse wall of the implant.

7. The implant of claim 3 wherein the barb extends from the end of each of the first arm segments adjacent the second arm segments.

8. The implant of claim 3 wherein the barb extends from the end of each of the second arm segments adjacent the first arm segments.

9. The implant of claim 3 wherein one of the barbs extends from the end of the first arm segment and the other barb extends from the end of the second arm segment.

10. An implant to fit within an intervertebral space formed between first and second vertebral members, the implant comprising:
    a body having a generally rectangular walled perimeter, the body including a height defined by a superior surface that contacts the first vertebral member and an inferior surface that contacts the second vertebral member, the body being substantially open at its superior and inferior ends; and
    a fixation mechanism, comprising:
        a screw having a screw head extending through a wall of the walled perimeter of the body and a threaded shaft extending into the interior of the body;
        an internally threaded ring provided about the threaded shaft of the screw; and
        a pair of arms hingedly connected to the ring, the pair of arms being disposed about the screw shaft in superior and inferior directions;
    such that upon rotation of the screw head from outside the implant, the ring moves toward the screw head thereby causing the pair of arms to move from a first position wherein the arms are within the walled perimeter of said body to a second position wherein a portion of said arms extend outside the walled perimeter of said body in the superior and inferior directions such that said portions of said arms extend into the first and second vertebral members to affix said implant within the intervertebral space therebetween.

11. The implant of claim 10, wherein the arms are positioned in a diametrically opposed fashion on either side of the screw and move simultaneously from the first position to the second position so as to contact the first and second vertebral members at approximately the same time to affix said implant within the intervertebral space between such first and second vertebral members.

12. The implant of claim 10, further comprising the fixation mechanism such that the head of the screw is operable from outside the perimeter of the implant, the screw having a non-threaded portion adjacent the screw head and a threaded portion extending distally away from the screw head, a collar is provided about the non-threaded portion of the screw, said collar being affixed to the anterior wall of the implant such that the head of the screw extends through said wall, each of the arms being hingedly connected to the collar and ring, each of the arms being provided with first and second arm segments hingedly connected together such that upon rotation of the screw head the ring moves toward the screw head such that each of the arms extend radially away from the screw shaft so that a portion of each of said arm segments extend outside the perimeter of the implant when the arms are in the second position.

13. The implant of claim 12, wherein when the fixation mechanism is in the second position, a portion of each arm segment that extends outside the perimeter of the implant is provided with a barb that can bite into the first and second vertebral members adjacent the implant to affix the implant within the vertebral space therebetween.

14. The implant of claim 13 wherein the barb extends from the end of each of the first arm segments which are adjacent the second arm segments.

15. The implant of claim 13 wherein the barb extends from the end of each of the second arm segments which are adjacent the first arm segments.

16. The implant of claim 13 wherein one of the barbs extends from the end of the first arm segment of one arm and the other barb extends from the end of the second arm segment of the other arm.

17. An implant to fit within an intervertebral space formed between first and second vertebral members, the implant comprising:
   a body including a superior surface to contact the first vertebral member and an inferior surface to contact the second vertebral member, the body including a generally rectangular walled perimeter open at its superior and inferior ends;
   a screw member with a screw head extending through a wall of the walled perimeter of the body, the screw having a non-threaded shaft portion adjacent the screw head and a threaded shaft portion distal to said screw head extending into the interior of the body;
   a collar provided about the non-threaded shaft portion of the screw, said collar being affixed to the wall of the implant;
   an internally threaded ring provided about the threaded shaft portion of the screw;
   a first and second arm hingedly connected to the collar and ring, each of the first and second arms being provided with first and second arm segments hingedly connected together so that the arm segments can bend relative to one another, the first and second arms being diametrically disposed about the screw shaft in the superior and inferior directions; and
   a barb being provided on an end of each of the first arm segments adjacent the second arm segments;
   such that upon rotation of the screw head from outside the implant, the ring moves toward the screw head thereby causing the first and second arm segments of the first and second arms to bend away from each other in the superior and inferior directions whereby when the arms segments are nearest the screw shaft the arm segments and barbs are totally within the perimeter of the walled perimeter of the implant, and when the arm segments have moved farthest away from the screw shaft a portion the arm segments and the barbs are outside the walled perimeter of the body to contact the first and second vertebral members to affix the implant with the intervertebral space between the first and second vertebral members.

18. An implant to fit within an intervertebral space between first and second vertebral members, the implant comprising:
   a body having a walled perimeter being substantially open at its superior and inferior ends, the body including a height defined by a superior surface that contacts the first vertebral member and an inferior surface that contacts the second vertebral member; and
   a fixation means, comprising:
      a screw having a screw head extending through a wall of the walled perimeter of the body and a threaded shaft extending into the interior of the body;
      an internally threaded ring provided about the threaded shaft of the screw; and
      a fixation portion hingedly connected to the ring:
   such that upon rotation of the screw head from outside the implant, the ring moves toward the screw head thereby causing the fixation portion to secure the implant between the first and second vertebral members, the fixation means being operable, once the implant has been surgically implanted between the first and second vertebral members, to extend a fixation portion thereof into the first and second vertebral members to affix the implant in place.

* * * * *